United States Patent
Sato et al.

(10) Patent No.: US 7,956,225 B2
(45) Date of Patent: Jun. 7, 2011

(54) POLYFLUORO-1-ALKENE AND METHOD FOR PRODUCING THE SAME

(75) Inventors: Katsuyuki Sato, Ibaraki (JP); Seiichiro Murata, Ibaraki (JP); Akihiko Ikeda, Ibaraki (JP); Yoshiyama Kaneumi, Ibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 12/993,564

(22) PCT Filed: Jun. 12, 2009

(86) PCT No.: PCT/JP2009/060732
§ 371 (c)(1),
(2), (4) Date: Nov. 19, 2010

(87) PCT Pub. No.: WO2009/151110
PCT Pub. Date: Dec. 17, 2009

(65) Prior Publication Data
US 2011/0077435 A1    Mar. 31, 2011

(30) Foreign Application Priority Data
Jun. 13, 2008 (JP) .................................. 2008-154916

(51) Int. Cl.
*C07C 17/00* (2006.01)
*C07C 21/18* (2006.01)
(52) U.S. Cl. ........................................ 570/155; 570/136
(58) Field of Classification Search .................. 570/136, 570/155
See application file for complete search history.

(56) References Cited

U.S. PATENT DOCUMENTS
4,613,708 A    9/1986    Riess et al.

FOREIGN PATENT DOCUMENTS
| | | |
|---|---|---|
| DE | 40 34 123 A1 | 4/1992 |
| JP | 58-174334 | 10/1983 |
| JP | 59-108081 | 6/1984 |

OTHER PUBLICATIONS

International Search Report from corresponding PCT application No. PCT/JP2009/060732 dated Sep. 15, 2009, 2 pgs.
International Preliminary Report on Patentability and Written Opinion from corresponding PCT application No. PCT/JP2009/060732, dated Jan. 11, 2011, 5 pgs.

*Primary Examiner* — Jafar Parsa
(74) *Attorney, Agent, or Firm* — Brinks Hofer Gilson & Lione

(57) ABSTRACT

A polyfluoro-1-alkene represented by the general formula: $CF_3(CF_2)_nCH_2(CF_2)_mCH=CH_2$ [I], wherein n is an integer of 0 to 5, and m is an integer of 1 to 7, is produced by reacting a polyfluoroalkyl iodide represented by the general formula: $CF_3(CF_2)_nCH_2(CF_2)_m(CH_2CH_2)I$ [II], wherein n is an integer of 0 to 5, and m is an integer of 1 to 7, with an inorganic basic compound in the presence of a phase transfer catalyst. Alternatively, the polyfluoro-1-alkene is produced by reacting the polyfluoroalkyl iodide [II] with a nitrogen-containing organic basic compound, and is obtained product [I] as one fraction thereof. By the copolymerization of the polyfluoro-1-alkene with other fluorinated olefin monomers, a fluorine-containing copolymer having excellent light transmittance in the visible light range is formed.

7 Claims, No Drawings

POLYFLUORO-1-ALKENE AND METHOD FOR PRODUCING THE SAME

RELATED APPLICATION

This application is a 35 U.S.C. §371 national phase filing of International Patent Application No. PCT/JP2009/060732, filed Jun. 12, 2009, through which and to which priority is claimed under 35 U.S.C. §119 to Japanese Patent Application No. 2008-154916, filed Jun. 13, 2008.

TECHNICAL FIELD

The present invention relates to a polyfluoro-1-alkene and a method for producing the same. More specifically, the present invention relates to a polyfluoro-1-alkene that is compounds having a perfluoroalkyl group containing 6 or less carbon atoms and that is used as a copolymerizable monomer in the production of fluorine-containing copolymers serving as active ingredients of, for example, water- and oil-repellents; and a method for producing the polyfluoro-1-alkene.

BACKGROUND ART

Acrylic acid derivatives of perfluoroalkyl alcohols (e.g., $CF_3(CF_2)_7CH_2CH_2OCOCH=CH_2$) are used in large amounts as monomers for synthesizing water- and oil-repellents for textile. Moreover, perfluoroalkyl alcohols serving as starting materials of the acrylates are widely used as, for example, surfactants (see Patent Document 1).

Such compounds having a perfluoroalkyl group as a structural unit are generally known to be able to improve surface modification properties, water- and oil-repellency, antifouling properties, mold-release properties, leveling properties, and other properties, when applied on the surfaces of fiber, metal, glass, rubber, resin, etc. Particularly, compounds having a $C_8$-$C_{12}$ perfluoroalkyl group (telomer compounds) are most likely to develop the aforementioned desired performance, and therefore, $C_8$ telomer compounds are particularly preferably used.

On the other hand, it is reported that in particular, telomer compounds having a $C_8$-$C_{12}$ perfluoroalkyl group are biologically degraded in the environment and converted to compounds having relatively high bioaccumulative and environmental concentration, causing concerns for exposure during treatment processes, and release or diffusion from waste, treated substrates, etc., into the environment. Moreover, compounds having a perfluoroalkyl group containing 14 or more carbon atoms are very difficult to handle because of their physicochemical properties, and hence, such compounds are rarely used in practice.

As for telomer compounds having a perfluoroalkyl group containing 8 or more carbon atoms, generation and incorporation of perfluorooctanoic acids with high bioaccumulation potential is unavoidable during the production of the telomer compounds.

For these reasons, companies that produce such telomer compounds have retreated from the production of the compounds or promoted the use of alternative compounds having a perfluoroalkyl group containing 6 or less carbon atoms. However, compounds having a perfluoroalkyl group containing 6 or less carbon atoms cause a significant decrease in orientation on the surface of a treated substrate, and the melting point, glass transition point, etc., of the compounds are markedly lower than those of $C_8$ compounds. Accordingly, the compounds are highly influenced by their using environmental conditions, such as temperature, humidity, stress, and the organic solvent, and the desired performance cannot be sufficiently achieved. In addition, durability and other properties are affected.

PRIOR ART DOCUMENT

PATENT DOCUMENT

Patent Document 1: JP-B-63-22237

OUTLINE OF THE INVENTION

PROBLEM TO BE SOLVED BY THE INVENTION

An object of the present invention is to provide a polyfluoro-1-alkene that is compounds having a perfluoroalkyl group in which the number of successive $CF_2$ groups is 5 or less, and that is effectively used as a copolymerizable monomer in the production of resinous or elastomeric fluorine-containing copolymers, which are used as active ingredients of surface-treating agents, such as water- and oil- repellents and mold-release agents; and to provide a method for producing the polyfluoro-1-alkene.

MEANS FOR SOLVING THE PROBLEM

The present invention provides a polyfluoro-1-alkene represented by the general formula:

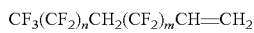

$$CF_3(CF_2)_nCH_2(CF_2)_mCH=CH_2 \quad [I]$$

wherein n is an integer of 0 to 5, and m is an integer of 1 to 7. The polyfluoro-1-alkene is produced by reacting a polyfluoroalkyl iodide represented by the general formula:

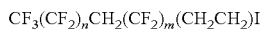

$$CF_3(CF_2)_nCH_2(CF_2)_m(CH_2CH_2)I \quad [II]$$

wherein n is an integer of 0 to 5, and m is an integer of 1 to 7, with an inorganic basic compound in the presence of a phase transfer catalyst. Alternatively, the polyfluoro-1-alkene is produced by reacting the polyfluoroalkyl iodide [II] with a nitrogen-containing organic basic compound, and is obtained product [I] as one fraction thereof.

EFFECT OF THE INVENTION

The polyfluoro-1-alkene of the present invention has an unsaturated structure that is vulnerable to ozone decomposition, when released into the environment, and can be easily decomposed into compounds with low environmental concentration and low bioaccumulation potential. Moreover, the polyfluoro-1-alkene does not produce environmental loading substances, such as perfluoroalkyl carboxylic acids, in the production process thereof.

Such an environmentally superior polyfluoro-1-alkene of the present invention can effectively be used as a copolymerizable monomer for the production of fluorine-containing copolymers that can improve performance such as surface modification properties, water- and oil-repellency, antifouling properties, mold-release properties, and leveling properties, which cannot be achieved or can be achieved only insufficiently by telomers having 6 or less carbon atoms, compared with $C_8$ telomers.

Furthermore, by the copolymerization of the polyfluoro-1-alkene with at least one of other fluorinated olefin monomers, such as tetrafluoroethylene, hexafluoropropylene, and vinylidene fluoride, a fluorine-containing copolymer having excellent light transmittance in the visible light range is provided. Such a fluorine-containing copolymer can be laminated on films, sheets, tubes, hoses, rods, blocks, belts, bottles, tanks, and other various substrates, without its excellent light transmittance being substantially impaired. The obtained composite can be suitably used in various applications, such as chemical tubes, fuel hoses, and anti-reflection films, for which high light transmittance, low refractive index, chemical resistance, dielectric resistance, etc., are required.

MODES FOR CARRYING OUT THE INVENTION

The polyfluoro-1-alkene of the present invention is produced as a product [I] by reacting a polyfluoroalkyl iodide represented by the general formula:

$$CF_3(CF_2)_nCH_2(CF_2)_m(CH_2CH_2)I \quad [II]$$

n: 0 to 5
m: 1 to 7 with a basic compound to carry out a terminal HI-elimination reaction.

The polyfluoroalkyl iodide, which is used as a starting material, can be obtained by the method shown in the Reference Examples described later.

The polyfluoroalkyl iodide can also be obtained by the addition reaction of terminally iodized polyfluoroalkane with ethylene. Examples of terminally iodized polyfluoroalkane include compounds of the following formulae:

$$CF_3(CF_2)(CH_2CF_2)I$$

$$CF_3(CF_2)_2(CH_2CF_2)I$$

$$CF_3(CF_2)_3(CH_2CF)I$$

$$CF_3(CF_2)_4(CH_2CF_2)I$$

$$CF_3(CF_2)(CH_2CF_2)(CF_2CF_2)I$$

$$CF_3(CF_2)(CH_2CF_2)(CF_2CF_2)_2I$$

$$CF_3(CF_2)(CH_2CF_2)(CF_2CF_2)_3I$$

$$CF_3(CF_2)_2(CH_2CF_2)(CF_2CF_2)I$$

$$CF_3(CF_2)_2(CH_2CF_2)(CF_2CF_2)_2I$$

$$CF_3(CF_2)_2(CH_2CF_2)(CF_2CF_2)_3I$$

The polyfluoroalkyl iodide of the general formula:

$$CF_3(CF_2)_nCH_2(CF_2)_m(CH_2CH_2)I \quad [II]$$

i.e., the general formula:

$$CH_3(CF_2)_n(CH_2CF_2)(CF_2CF_2)_p(CH_2CH_2)I \quad (m=2p+1)$$

can be produced by the addition reaction of a terminally iodized compound represented by the general formula:

$$CF_3(CF_2)_n(CH_2CF_2)(CF_2CF_2)_pI, \quad [A]$$

with ethylene.

The ethylene addition reaction is carried out in such a manner that the above compound [A] is subjected to an addition reaction with pressurized ethylene in the presence of a peroxide initiator. The number of addition is 1 or more, and preferably 1, although depending on the reaction conditions. Although the reaction temperature depends on the degradation temperature of the initiator used, the reaction is generally conducted at about 80 to 120° C.; when a peroxide initiator that decomposes at a low temperature is used, the reaction can be conducted at 80° C. or below. As a peroxide initiator, tert-butyl peroxide, di(tert-butylcyclohexyl)peroxy dicarbonate, dicetyl-peroxy dicarbonate, or the like may be used at a ratio of about 1 to 5 mol % based on the amount of compound [A].

The polyfluoroalkane iodide [II] is reacted with a basic compound to carry out dehydrohalogenation, thereby resulting in an HI-elimination reaction at position 1. Thus, a polyfluoro-1-alkene [I] is produced.

The HI-elimination reaction at position 1 is carried out by reacting the polyfluoroalkyl iodide [II] with an inorganic basic compound in the presence of a phase transfer catalyst, or by reacting the polyfluoroalkyl iodide [II] with a nitrogen-containing organic basic compound. The former method is preferably used, so that a polyfluoro-1-alkene having a purity as high as 99% is obtained with high yield. In this case, it is essential to use a phase transfer catalyst in combination with an inorganic basic compound. When no phase transfer catalyst is used, the HI-elimination reaction can hardly proceed.

Examples of inorganic basic compounds include lithium hydroxide, sodium hydroxide, potassium hydroxide, magnesium hydroxide, calcium hydroxide, and other monovalent or divalent metal hydroxides; sodium carbonate, sodium hydrogen carbonate, potassium carbonate, potassium hydrogen carbonate, and other monovalent or divalent metal carbonates; and the like. As a phase transfer catalyst to be used in combination with such an inorganic basic compound, a quaternary onium salt, Crown ether, or the like is used in an amount of about 0.01 to 10 mol %, and preferably about 0.1 to 3 mol %, based on the amount of inorganic basic compound.

The quaternary onium salt used is at least one of ammonium and phosphonium salts represented by the following general formulae:

$$(R_1R_2R_3R_4N)^+X^-$$

$$(R_1R_2R_3R_4P)^+X^-$$

R1 to R4: a $C_{1-25}$ alkyl, alkoxy, aryl, alkyaryl, aralkyl, or polyoxyalkylene group; or two or three of these groups can be taken together with N or P to form a heterocyclic structure $X^-$: $Cl^-$, $Br^-$, $HSO_4^-$, $H_2PO_4^-$, $RCOO^-$, $ROSO_2^-$, $RSO^-$, $ROPO_2H^-$, $CO_3^-$, or other anion Specific examples thereof include tetraethylammonium bromide, tetrabutylammonium chloride, tetrabutylammonium bromide, tetrabutylammonium iodide, n-dodecyltrimethylammonium bromide, cetyldimethylbenzylammonium chloride, methylcetyldibenzylammonium bromide, cetyldimethylethylammonium bromide, octadecyltrimethylammonium bromide, cetylpyridinium chloride, cetylpyridinium bromide, cetylpyridinium iodide, cetylpyridinium sulfate, 1-benzylpyridinium chloride, 1-benzyl-3,5-dimethylpyridinium chloride, 1-benzyl-4-phenylpyridinium chloride, 1,4-dibenzylpyridinium chloride, 1-benzyl-4-(pyrrolidinyl)pyridinium chloride, 1-benzyl-4-pyridinopyridinium chloride, tetraethylammonium acetate, trimethylbenzylammonium benzoate, trimethylbenzylammonium-p-toluene sulfonate, trimethylbenzylammonium borate, 8-benzyl-1,8-diazabicyclo[5,4,0]-undec-7-enium chloride, 1,8-diazabicyclo[5,4,0]-undecene-7-methylammonium methosulfate, 5-benzyl-1,5-diazabicyclo[4,3,0]-5-nonenium chloride, 5-benzyl-1,5-diazabicyclo[4,3,0]-5-nonenium bromide, 5-benzyl-1,5-diazabicyclo[4,3,0]-5-nonenium tetrafluoroborate, 5-benzyl-1,5-diazabicyclo[4,3,0]-5-nonenium hexafluorophosphate, and other quaternary ammonium salts; tetraphenylphosphonium chloride, triphenylbenzylphosphonium chloride, triphenylbenzylphosphonium bromide, triphenylmethoxymethylphosphonium chloride, triphenylmethylcarbonylmethylphosphonium chloride, triphenylethoxycarbonylmethylphosphonium chloride, trioctylbenzylphosphonium chloride, trioctylmethylphosphonium bromide, trioctylethylphosphonium acetate, trioctylethylphosphonium dimethylphosphate, tetraoctylphosphonium chloride, cetyldimethylbenzylphosphonium chloride, and other quaternary phosphonium salts.

Examples of nitrogen-containing organic basic compounds include diethylamine, triethylamine, pyridine or derivatives thereof, diethanolamine, triethanolamine, 1,8-diazabicyclo[5.4.0]-7-undecene, diazabicyclononene, and the like. Preferably, 1,8-diazabicyclo[5.4.0]-7-undecene having low nucleophilicity is used.

In a case of a nitrogen-containing organic basic compound is used, a large amount of polyfluoroalkadiene mixture is produced as a by-product, in addition to the target polyfluoro-1-alkene, as shown in Examples 2 to 4 described later; however, the polyfluoro-1-alkene and the polyfluoroalkadiene mixture can be separated by fractional distillation by difference in vapor temperature during vacuum distillation.

Such an inorganic or organic basic compound is used in a molar ratio of about 0.1 to 10, preferably 0.95 to 2.5, and more preferably 1.0 to 1.5, with respect to the polyfluoroalkane iodide [II]. When the amount of basic compound is less than this range, the desired HI-elimination reaction does not proceed smoothly; whereas when the amount of basic compound is more than this range, the removal of the basic compound becomes difficult, and side reactions is caused, resulting in an increased amount of waste.

Although the HI-elimination reaction can be carried out in the absence of a solvent, the reaction is preferably carried out in the presence of an aqueous solvent or an organic solvent in terms of reaction efficiency and control of heating generation. Generally, water is used an aqueous solvent. Examples of organic solvents include alcohols, such as methanol, ethanol, propanol, and isopropanol; ethers, such as diethyl ether, 1,4-dioxane, and tetrahydrofuran; ketones, such as acetone, methyl ethyl ketone, and methyl isobutyl ketone; hydrocarbons, such as toluene and cyclohexane; aprotic polar solvents, such as acetonitrile, N,N-dimethylformamide, N,N-diethylformamide, N,N-dimethylacetamide, N,N-diethylacetamide, and N-methyl-2-pyrrolidone; and fluorine-containing organic solvents, such as hydrochlorofluorocarbon (e.g., HCFC-225) and hydrofluoroether (e.g., Novec HFE; a product of 3M).

An aqueous solvent or an organic solvent is used in a volume ratio of about 0.1 to 100, preferably about 1 to 10, and more preferably 3 to 6, with respect to the polyfluoroalkane iodide [II]. However, a larger amount of solvent does not affect the reaction efficiency, and thus the solvent is preferably used in a volume ratio of 3 to 6.

The HI-elimination reaction is carried out at about −20 to 100° C., and preferably about −10 to 80° C. Side reactions proceed at temperatures higher than this range, generating a large amount of by-products with an unknown structure. The reaction may be carried out at reduced pressure, atmospheric pressure, or increased pressure; in terms of ease of handling the reaction apparatus, the reaction is preferably carried out under atmospheric pressure.

In a case of static phase separation is performed after the reaction is completed, the separated organic layer is washed with water, for example, to remove the basic compound, and purification is then performed by distillation etc., according to a standard method, thereby obtaining the target polyfluoro-1-alkene. For example, in a case of a polar solvent is used instead of performing static phase separation, the solvent is distilled off under reduced pressure, followed by the same treatment as in the case where static phase separation is carried out.

EXAMPLES

The following describes the present invention with reference to Examples.

Reference Example 1

A compound of the formula: $CF_3(CF_2)_3(CH_2CF_2)(CF_2CF_2)_2I$ (99GC %) (603 g; 0.99 mol) and 7 g (0.05 mol) of di-tert-butyl peroxide were placed in a 1200-ml autoclave equipped with a stirrer and thermometer, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 41 g (1.45 mol) of ethylene was introduced over about 3 hours. The content was collected at an internal temperature of 50° C. or less, thereby obtaining 637 g (yield: 98.8%) of a compound of the formula: $CF_3(CF_2)_3(CH_2CF_2)(CF_2CF_2)_2(CH_2CH_2)I$ (98GC %), i.e., the formula: $C_4F_9CH_2(CF_2)_5CH_2CH_2I$.

Example 1

In a 50-ml glass reactor equipped with a cooling condenser, thermocouple, and magnet stirrer, 3,3,4,4,5,5,6,6,7,7,9,9,10,10,11,11,12,12,12-nonadecafluoro-1-iodododecane of the formula: $C_4F_9CH_2(CF_2)_5CH_2CH_2I$ (5 g; 7.8 mmol) obtained in above Reference Example 1 was suspended in an aqueous solution, in which 0.34 g (8.5 mmol) of sodium hydroxide and 0.03 g (0.13 mmol) of tetrabutylammonium chloride were dissolved in 15 ml of water. The mixture was reacted by continuous stirring for about 72 hours at room temperature.

After the reaction was completed, the lower layer obtained by static phase separation was washed twice with 20 ml of water and then once with a saturated saline solution. The obtained reaction solution was dehydrated and dried over anhydrous magnesium sulfate. The recovered solution was purified by vacuum distillation, thereby obtaining 3.2 g (yield: 80%) of product A as a fraction with a vapor temperature of 76 to 77° C./1 kPa (purity: 99%). The structure of the obtained fraction was determined by $^{19}F$-NMR and $^1H$-NMR.

Product A: 3,3,4,4,5,5,6,6,7,7,9,9,10,10,11,11,12,12,12-nonadecafluoro-1-dodecene
$CF_3CF_2CF_2CF_2CH_2CF_2CF_2CF_2CF_2CF_2CH=CH_2$
$^1H$-NMR (CDCl$_3$, TMS): δ2.89 (CH$_2$CF$_2$) 5.79 (CH=CH$_2$) 5.97 (CH=CH$_2$)
$^{19}F$-NMR (CDCl$_3$, C$_6$F$_6$): ppm −82.1 (CF$_3$) −126.9 (CF$_3$CF$_2$CF$_2$CF$_2$) −124.8 (CF$_3$CF$_2$CF$_2$CF$_2$) −113.2 (CF$_2$CH$_2$CF$_2$) −113.0 (CF$_2$CH$_2$CF$_2$) −121.7 (CH$_2$CF$_2$CF$_2$CF$_2$) −124.2 (CH$_2$CF$_2$CF$_2$CF$_2$) −124.6 (CF$_2$CF$_2$CH=CH$_2$) −114.8 (CF$_2$CF$_2$CH=CH$_2$)

Example 2

3,3,4,4,5,5,6,6,7,7,9,9,10,10,11,11,12,12,12-nonadecafluoro-1-iodododecane of the formula: $C_4F_9CH_2(CF_2)_5CH_2CH_2I$ (5 g; 7.8 mmol) obtained in above Reference Example 1 was dissolved in 15 ml of fluorine-containing organic solvent (AK-225; a product of Asahi Glass), and the resulting solution was placed in a 50-ml glass reactor equipped with a cooling condenser, thermocouple, and magnet stirrer. After ice-cooling, 1.3 g (8.5 mmol) of 1,8-diazabicyclo[5.4.0]-7-undecene [DBU] was added dropwise, while maintaining the internal temperature in the range of 0 to 10° C. After the completion of addition, the mixture was stirred at about 0° C. for about 1 hour, and stirring was then continued at room temperature for about 23 hours (total reaction time: 24 hours).

After the reaction was completed, washing with 20 ml of water was performed twice, and subsequently washing with a saturated saline solution was performed once. The obtained reaction solution was dehydrated and dried over anhydrous magnesium sulfate. After the reaction solvent was distilled off under reduced pressure, the residue was purified by distillation under reduced pressure, thereby obtaining 1.2 g (yield: 33%) of a fraction with a vapor temperature of 68 to 70° C/1 kPa. The structure of the obtained fraction was determined by $^{19}$F-NMR and $^1$H-NMR, and the fraction was identified as a mixture of products B and C having a weight ratio of about 48:52. Subsequently, 0.6 g (yield: 15%) of product A was obtained as a fraction with a vapor temperature of 76 to 77° C./1 kPa (purity: 98%).

Product B: 3,3,4,4,5,5,6,6,7,7,9,10,10,11,11,12,12,12-octadecafluorododeca-1,8-diene

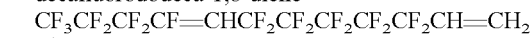

Product C: 3,3,4,4,5,5,6,6,7,9,9,10,10,11,11,12,12,12-octadecafluorododeca-1,7-diene

$^1$H-NMR: TMS Product B δ=5.81 (1H:—CF═CH—), 5.79 (1H:—CF$_2$—CH═), 5.97 (2H:═CH$_2$) Product C δ=5.81 (1H:—CH═CF—), 5.79 (1H:—CF$_2$—CH═), 5.97 (2H:═CH$_2$)

$^{19}$F-NMR: CFCl$_3$ Product B δ=−79.95 (3F:CF$_3$—), −108.35 (2F:═CHCF$_2$—), −111.34 (1F:—CF═), −112.34 (2F:—CF$_2$CH═), −117.4 to 126.3 (10F:—CF$_2$—) Product C δ=−80.20 (3F:CF$_3$—), −108.35 (2F:═CHCF$_2$—), −109.81 (1F:—CF═), −112.34 (2F:—CF$_2$CH═), −117.4 to 126.3 (10F:—CF$_2$—)

Example 3

In Example 2, 1.8 g (17.3 mmol) of triethylamine was used in place of DBU, and the total reaction time was changed to 48 hours. Then, the reaction was carried out, thereby obtaining 2.0 g (yield: 55%) of mixture of products B and C (weight ratio: 49:51), which was the above fraction, and 1.0 g (yield: 26%) of product A (purity: 98%), which was the above fraction.

Example 4

In Example 3, the amount of triethylamine was changed to 0.9 g (8.5 mmol), and 15 ml of tetrahydrofuran was used as a solvent in place of the fluorine-containing organic solvent. Then, the reaction was carried out, thereby obtaining 1.8 g (yield: 46%) of product A (purity: 98%) as the above fraction.

Reference Example 2

A compound of the formula: CF$_3$(CF$_2$)$_3$(CH$_2$CF$_2$)(CF$_2$CF$_2$)I (99.3GC %) (609 g; 1.19 mol) and 6 g of di-tert-butyl peroxide were placed in a 1200-ml autoclave equipped with a stirrer and thermometer, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 50 g (1.79 mol) of ethylene was introduced over about 3 hours. The content was collected at an internal temperature of 50° C. or less, thereby obtaining 640 g (yield: 97.3%) of a compound of the formula: CF$_3$(CF$_2$)$_3$(CH$_2$CF$_2$)(CF$_2$CF$_2$)(CH$_2$CH$_2$)I (97.4GC %).

Example 5

In Example 1, 4.2 g of the polyfluoroalkyl iodide of the formula: CF$_3$(CF$_2$)$_3$(CH$_2$CF$_2$)(CF$_2$CF$_2$)(CH$_2$CH$_2$)I═C$_4$F$_9$CH$_2$(CF$_2$)$_3$CH$_2$CH$_2$I obtained in above Reference Example 2 was used in place of the compound of the formula: CF$_3$(CF$_2$)$_3$(CH$_2$CF$_2$)(CF$_2$CF$_2$)$_2$(CH$_2$CH$_2$)I═C$_4$F$_9$CH$_2$(CF$_2$)$_5$CH$_2$CH$_2$I. Thus, 2.6 g (yield: 81%) of a compound of the formula: C$_4$F$_9$CH$_2$(CF$_2$)$_3$CH═CH$_2$, which was a fraction with a vapor pressure of 63 to 65° C./1 kPa, was obtained as a product D.

Product D: 3,3,4,4,5,5,7,7,8,8,9,9,10,10,10-pentadecafluoro-1-decene

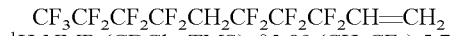

$^1$H-NMR (CDCl$_3$, TMS): δ2.89 (CH$_2$CF$_2$) 5.79 (CH═CH$_2$) 5.97 (CH═CH$_2$)

$^{19}$F-NMR (CDCl$_3$, C$_6$F$_6$): ppm −82.0 (CF$_3$) −126.7 (CF$_3$CF$_2$CF$_2$) −124.9 (CF$_3$CF$_2$CF$_2$) −113.0 (CF$_2$CH$_2$CF$_2$) −111.5 (CF$_2$CH$_2$CF$_2$) −111.8 (CH$_2$CF$_2$CF$_2$) −114.8 (CH$_2$CF$_2$CF$_2$CF$_2$)

Reference Example 3

A compound of the formula: CF$_3$(CF$_2$)$_3$(CH$_2$CF$_2$)(CF$_2$CF$_2$)$_3$I (98GC %) (500 g; 0.69 mol) and 7 g of di-tert-butyl peroxide were placed in a 1200-ml autoclave equipped with a stirrer and thermometer, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 23 g (0.95 mol) of ethylene was introduced over about 3 hours. The content was collected at an internal temperature of 50° C. or less, thereby obtaining 515 g (yield: 98.6%) of a compound of the formula: CF$_3$(CF$_2$)$_3$(CH$_2$CF$_2$)(CF$_2$CF$_2$)$_3$(CH$_2$CH$_2$)I (96GC %), i.e., the formula: C$_4$F$_9$CH$_2$(CF$_2$)$_7$CH$_2$CH$_2$I.

Example 6

In Example 1, 5.8 g of the polyfluoroalkyl iodide of the formula: CF$_3$(CF$_2$)$_3$(CH$_2$CF$_2$)(CF$_2$CF$_2$)$_3$(CH$_2$CH$_2$)I═C$_4$F$_9$CH$_2$(CF$_2$)$_7$CH$_2$CH$_2$I obtained in above Reference Example 3 was used in place of the compound of the formula: CF$_3$(CF$_2$)$_3$(CH$_2$CF$_2$)(CF$_2$CF$_2$)$_2$(CH$_2$CH$_2$)I═C$_4$F$_9$CH$_2$(CF$_2$)$_5$CH$_2$CH$_2$I. Thus, 3.0 g (yield: 63%) of a compound of the formula: C$_4$F$_9$CH$_2$(CF$_2$)$_7$CH═CH$_2$, which was a fraction with a vapor pressure of 90 to 94° C./1 kPa, was obtained as a product E.

Product E: 3,3,4,4,5,5,6,6,7,7,8,8,9,9,11,11,12,12,13,13,14,14,14-tricosafluoro-1-tetradecene

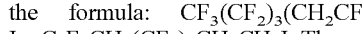

$^1$H-NMR (CDCl$_3$, TMS): δ2.89 (CH$_2$CF$_2$) 5.79 (CH═CH$_2$) 5.97 (CH═CH$_2$)

$^{19}$F-NMR(CDCl$_3$, C$_6$F$_6$): ppm −82.1 (CF$_3$) −126.9 (CF$_3$CF$_2$CF$_2$) −124.8 (CF$_3$CF$_2$CF$_2$CF$_2$) −113.4 (C F$_2$CH$_2$CF$_2$) −113.0 (CF$_2$CH$_2$CF$_2$) −121.7 (CH$_2$CF$_2$CF$_2$CF$_2$) −122.7 (CH$_2$CF$_2$CF$_2$CF$_2$) −124.3 (CF$_2$CF$_2$CF$_2$CF$_2$CH=CH$_2$) −122.6 (CF$_2$CF$_2$CF$_2$CF$_2$CH=CH$_2$) −122.9 (CF$_2$CF$_2$CF$_2$CF$_2$CH=CH$_2$) −114.8 (CF$_2$CF$_2$CF$_2$CF$_2$CH=CH$_2$)

Reference Example 4

A compound of the formula: CF$_3$CF$_2$(CH$_2$CF$_2$)(CF$_2$CF$_2$)I (99.8GC %) (610 g; 1.48 mol) and 7 g of di-tert-butyl peroxide were placed in a 1200-ml autoclave equipped with a stirrer and thermometer, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 62 g (2.23 mol) of ethylene was introduced over about 3 hours. The content was collected at an internal temperature of 50° C. or less, thereby obtaining 644 g (yield: 98.0%) of a compound of the formula: CF$_3$CF$_2$(CH$_2$CF$_2$)(CF$_2$CF$_2$)(CH$_2$CH$_2$)I (98.7GC %).

Example 7

In Example 1, 3.4 g of the polyfluoroalkyl iodide of the formula: CF$_3$(CF$_2$)(CH$_2$CF$_2$)(CF$_2$CF$_2$)(CH$_2$CH$_2$)I=C$_2$F$_5$CH$_2$(CF$_2$)$_3$CH$_2$CH$_2$I obtained in above Reference Example 4 was used in place of the compound of the formula: CF$_3$(CF$_2$)$_3$(CH$_2$CF$_2$)(CF$_2$CF$_2$)$_2$(CH$_2$CH$_2$)I=C$_4$F$_9$CH$_2$(CF$_2$)$_5$CH$_2$CH$_2$I. Thus, 2.1 g (yield: 87%) of a compound of the formula: C$_2$F$_5$CH$_2$(CF$_2$)$_3$CH=CH$_2$, which was a fraction with a vapor pressure of 52 to 55° C./1 kPa, was obtained as a product F.
Product F: 3,3,4,4,5,5,7,7,8,8,8-undecafluoro-1-octene
CF$_3$CF$_2$CH$_2$CF$_2$CF$_2$CF$_2$CH=CH$_2$
$^1$H-NMR (CDCl$_3$, TMS): δ2.89 (CH$_2$CF$_2$) 5.79 (CH=CH$_2$) 5.97 (CH=CH$_2$)
$^{19}$F-NMR (CDCl$_3$, C$_6$F$_6$): ppm −87.1 (CF$_3$) −116.8 (CF$_3$CF$_2$CH$_2$CF$_2$) −111.6 (CF$_3$CF$_2$CH$_2$CF$_2$) −111.9 (CF$_2$CF$_2$CH=CH$_2$) −114.8 (CF$_2$CF$_2$CH=CH$_2$)

Reference Example 5

A compound of the formula: CF$_3$CF$_2$(CH$_2$CF$_2$)(CF$_2$CF$_2$)$_2$I (99.4GC %) (605 g; 1.18 mol) and 6 g of di-tert-butyl peroxide were placed in a 1200-ml autoclave equipped with a stirrer and thermometer, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 50 g (1.79 mol) of ethylene was introduced over about 3 hours. The content was collected at an internal temperature of 50° C. or less, thereby obtaining 639 g (yield: 98.0%) of a compound of the formula: CF$_3$CF$_2$(CH$_2$CF$_2$)(CF$_2$CF$_2$)$_2$(CH$_2$CH$_2$)I (97.3GC %).

Example 8

In Example 1, 4.2 g of the polyfluoroalkyl iodide of the formula: CF$_3$(CF$_2$)(CH$_2$CF$_2$)(CF$_2$CF$_2$)$_2$(CH$_2$CH$_2$)I=C$_2$F$_5$CH$_2$(CF$_2$)$_5$CH$_2$CH$_2$I obtained in above Reference Example 5 was used in place of the compound of the formula: CF$_3$(CF$_2$)$_3$(CH$_2$CF$_2$)(CF$_2$CF$_2$)$_2$(CH$_2$CH$_2$)I=C$_4$F$_9$CH$_2$(CF$_2$)$_5$CH$_2$CH$_2$I. Thus, 2.5 g (yield: 78%) of a compound of the formula: C$_2$F$_5$CH$_2$(CF$_2$)$_5$CH=CH$_2$, which was a fraction with a vapor pressure of 63 to 65° C./1 kPa, was obtained as a product G.
Product G: 3,3,4,4,5,5,6,6,7,7,9,9,10,10,10-pentadecafluoro-1-decene
CF$_3$CF$_2$CH$_2$CF$_2$CF$_2$CF$_2$CF$_2$CH=CH$_2$
$^1$H-NMR (CDCl$_3$, TMS): δ2.89 (CH$_2$CF$_2$) 5.79 (CH=CH$_2$) 5.97 (CH=CH$_2$)
$^{19}$F-NMR (CDCl$_3$, C$_6$F$_6$): ppm −87.1 (CF$_3$) −116.8 (CF$_3$CF$_2$CH$_2$CF$_2$) −113.0 (CF$_3$CF$_2$CH$_2$CF$_2$) −121.5 (CH$_2$CF$_2$CF$_2$) −124.1 (CH$_2$CF$_2$CF$_2$CF$_2$) −124.2 (CF$_2$CF$_2$CH=CH$_2$) −114.8 (CF$_2$CF$_2$CH=CH$_2$)

Reference Example 6

A compound of the formula: CF$_3$CF$_2$(CH$_2$CF$_2$)(CF$_2$CF$_2$)$_3$I (98.7GC %) (605 g; 0.98 mol) and 7 g of di-tert-butyl peroxide were placed in a 1200-ml autoclave equipped with a stirrer and thermometer, and the autoclave was degassed by a vacuum pump. After the internal temperature was raised to 80° C. by heating, ethylene was sequentially introduced so that the internal pressure was 0.5 MPa. When the internal pressure dropped to 0.2 MPa, ethylene was introduced again to return the pressure to 0.5 MPa; this operation was repeated. While maintaining the internal temperature at 80 to 115° C., 43 g (1.53 mol) of ethylene was introduced over about 3 hours. The content was collected at an internal temperature of 50° C. or less, thereby obtaining 630 g (yield: 98.5%) of a compound of the formula: CF$_3$CF$_2$(CH$_2$CF$_2$)(CF$_2$CF$_2$)$_3$(CH$_2$CH$_2$)I (97.7GC %).

Example 9

In Example 1, 5.0 g of the polyfluoroalkyl iodide of the formula: CF$_3$(CF$_2$)(CH$_2$CF$_2$)(CF$_2$CF$_2$)$_3$(CH$_2$CH$_2$)I=C$_2$F$_5$CH$_2$(CF$_2$)$_7$CH$_2$CH$_2$I obtained in above Reference Example 6 was used in place of a compound of the formula: CF$_3$(CF$_2$)$_3$(CH$_2$CF$_2$)(CF$_2$CF$_2$)$_2$(CH$_2$CH$_2$)I=C$_4$F$_9$CH$_2$(CF$_2$)$_5$CH$_2$CH$_2$I. Thus, 2.0 g (yield: 50%) of a compound of the formula: C$_2$F$_5$CH$_2$(CF$_2$)$_7$CH=CH$_2$, which was a fraction with a vapor pressure of 75 to 77° C./1 kPa, was obtained as a product H.
Product H: 3,3,4,4,5,5,6,6,7,7,8,8,9,9,11,11,12,12,12-nonadecafluoro-1-dodecene
CF$_3$CF$_2$CH$_2$CF$_2$CF$_2$CF$_2$CF$_2$CF$_2$CF$_2$CH=CH$_2$
$^1$H-NMR (CDCl$_3$, TMS): δ2.89 (CH$_2$CF$_2$) 5.79 (CH=CH$_2$) 5.97 (CH=CH$_2$)
$^{19}$F-NMR (CDCl$_3$, C$_6$F$_6$): ppm −87.1 (CF$_3$) −116.8 (CF$_3$CF$_2$CH$_2$CF$_2$) −113.0 (CF$_3$CF$_2$CH$_2$CF$_2$) −121.7 (CH$_2$CF$_2$CF$_2$) −122.7 (CH$_2$CF$_2$CF$_2$CF$_2$) −124.2 (CF$_2$CF$_2$CF$_2$CF$_2$CH=CH$_2$) −122.4 (CF$_2$CF$_2$CF$_2$CH=CH$_2$) −122.7 (CF$_2$CF$_2$CF$_2$CH=CH$_2$) −114.8 (CF$_2$CF$_2$CF$_2$CF$_2$CH=CH$_2$)

Comparative Example

When tetrabutylammonium chloride was not used as a phase transfer catalyst in Example 1, only 0.1 g (yield: 3%) of product A (purity: 97%) was obtained as the above fraction, and most of the starting materials were recovered without being reacted.

Reference Example 7

A 500-ml SUS316 autoclave equipped with a stirrer was degassed to vacuum. Then, 330 g of a perfluoro(2-n-butyltetrahydrofuran) solvent was placed therein, and the air in the autoclave was removed and replaced by nitrogen. Tetrafluoroethylene [TFE] (20 g; 67 mol %) and 50 g (33 mol %) of the product A (nonadecafluoro-1-dodecene) obtained in Example 1 were added thereto. After warming to 50° C., the internal pressure of the autoclave was 0.62 MPa•G.

Subsequently, 3 g of 25 wt. % AK225 (CF$_3$CF$_2$CHCl$_2$/CClF$_2$CF$_2$CHClF (45/55 wt. %) mixed solvent) solution of isobutyryl peroxide was introduced as an initiator using a metering pump to initiate a polymerization reaction. The polymerization reaction was carried out for 20 hours until the internal pressure reached 0.30 MPa•G. The obtained slurry was added to n-hexane, followed by filtration and drying, thereby obtaining 21 g of fluorine-containing copolymer.

(The properties of the obtained fluorine-containing copolymer)

Copolymerization composition ratio: TFE/product A=55/45 (wt. %), measured by $^{19}$F NMR Number average molecular weight Mn: 9500 GPC measurement was performed using Shodex GPC KD-805+KD-803+KD-G in a tetrahydrofuran eluate (based on polystyrene standards)

Light transmittance: 95% or more the light transmittance of a 100-μm-thick film was measured at a wavelength of 400 to 800 nm using a Jasco UV-visible spectrophotometer Reference Example 8

In Reference Example 7, the amounts of charged comonomers after degassing and nitrogen substitution were changed as follows: TFE: 20 g (54.4 mol %), vinylidene fluoride [VdF]: 3.3 g (14.0 mol %), and product A: 59.3 g (31.6 mol %). Thereby, 25 g of fluorine-containing copolymer was obtained. In the copolymer, the copolymerization composition of TFE/VdF/product A was 50/7/43 (wt. %), the number average molecular weight Mn was 11000, and the light transmittance was 95% or more.

Reference Example 9

In Reference Example 7, the amounts of charged comonomers after degassing and nitrogen substitution were changed as follows: vinylidene fluoride [VdF]: 20 g (70 mol %), and product A: 41.5 g (30 mol %). Thereby, 22 g of fluorine-containing copolymer was obtained. In the copolymer, the copolymerization composition of VdF/product A was 54/46 (wt. %), the number average molecular weight Mn was 21000, and the light transmittance was 95% or more.

The invention claimed is:

1. A polyfluoro-1-alkene represented by the general formula:

$$CF_3(CF_2)_nCH_2(CF_2)_mCH\!=\!CH_2 \qquad [I]$$

wherein n is an integer of 0 to 5, and m is an integer of 1 to 7.

2. A method for producing a polyfluoro-1-alkene represented by the general formula:

$$CF_3(CF_2)_nCH_2(CF_2)_nCH\!=\!CH_2 \qquad [I]$$

wherein n is an integer of 0 to 5, and m is an integer of 1 to 7, the method comprising reacting a polyfluoroalkyl iodide represented by the general formula:

$$CF_3(CF_2)_nCH_2(CF_2)_m(CH_2CH_2)I \qquad [II]$$

wherein n is an integer of 0 to 5, and m is an integer of 1 to 7, with an inorganic basic compound in the presence of a phase transfer catalyst.

3. The method for producing a polyfluoro-1-alkene according to claim 2, wherein the phase transfer catalyst is a quaternary onium salt.

4. The method for producing a polyfluoro-1-alkene according to claim 2, wherein the reaction is carried out in an aqueous solvent.

5. A method for producing a polyfluoro-1-alkene represented by the general formula:

$$CF_3(CF_2)_nCH_2(CF_2)_mCH\!=\!CH_2 \qquad [I]$$

wherein n is an integer of 0 to 5, and m is an integer of 1 to 7, the method comprising reacting a polyfluoroalkyl iodide represented by the general formula:

$$CF_3(CF_2)_nCH_2(CF_2)_m(CH_2CH_2)I \qquad [II]$$

wherein n is an integer of 0 to 5, and m is an integer of 1 to 7, with a nitrogen-containing organic basic compound to form a reaction mixture and collecting the polyfluoro-1-alkene as a fraction of the reaction mixture.

6. The method for producing a polyfluoro-1-alkene according to claim 5, wherein the nitrogen-containing organic basic compound is 1,8-diazabicyclo[5.4.0]-7-undecen.

7. The method for producing a polyfluoro-1-alkene according to claim 5, wherein the nitrogen-containing organic basic compound is triethylamine.

* * * * *